United States Patent [19]

Allan et al.

[11] Patent Number: 4,833,126
[45] Date of Patent: May 23, 1989

[54] PHARMACOLOGICALLY ACTIVE COMPOUNDS AND USE

[75] Inventors: Geoffrey Allan; John J. Adcock; Terence W. Smith, all of Beckenham, England

[73] Assignee: Burroughs Wellcome Co., Research Triangle Park, N.C.

[21] Appl. No.: 95,817

[22] Filed: Sep. 11, 1987

[30] Foreign Application Priority Data

Sep. 12, 1986 [GB] United Kingdom ............... 8622090

[51] Int. Cl.$^4$ ............................................. A61K 37/02
[52] U.S. Cl. ..................................... 514/18; 530/331; 514/826
[58] Field of Search .................. 514/18, 826; 530/331

[56] References Cited

U.S. PATENT DOCUMENTS 4,242,329  12/1980  Claeson et al. .................. 530/314

Primary Examiner—Delbert R. Phillips
Attorney, Agent, or Firm—Donald Brown

[57] ABSTRACT

The peptides of the formula

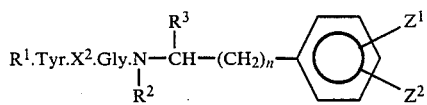

together with their pharmacologically acceptable salts, which have been described as exhibiting analgesic, antidiarrhoeal and antitussive activity, are effective in reversing neuronally-mediated bronchoconstriction in mammals. The said compounds have application in the palliation of conditions characterized by such a state, in particular asthma in human beings.

13 Claims, No Drawings

PHARMACOLOGICALLY ACTIVE COMPOUNDS AND USE

This invention relates to compounds useful in medicine, to pharmaceutical formulations containing such compounds and the preparation thereof, and to the use of the compounds in medicine.

The present invention more particularly relates to the peptides of formula (I)

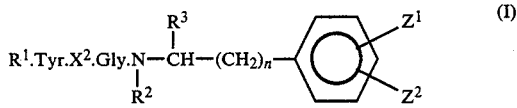

as hereinafter defined, together with pharmacologically acceptable salts thereof, which have been described as exhibiting analgesic, antidiarrhoeal and antitussive activity when investigated according to standard pharmacological procedures; see EP-A-0 127 154.

It has now surprisingly been found that the said compounds have an effect—reversal of neuronally—mediated bronchoconstriction, i.e. bronchodilatation—unrelated to those apparent from their previously taught, opioid properties and are in consequence of value, in both human and veterinary medicine, in a yet further, entirely distinct clinical area.

The compounds thus have application in the palliation of conditions characterised by such bronchoconstriction (bronchospasm), in particular asthma (including status asthmaticus) such as that induced by exercise, local irritation of the airways or stress, allergic asthma and intrinsic asthma.

Whereas the prototype opioid, morphine, has been proposed for use in the sedation of human patients with asthma or status asthmaticus to facilitate artificially assisted (mechanical) ventilation procedures, such a view has not found general favour and has been criticized, inter alia on the ground that such agents themselves cause bronchoconstriction and thus have the potential to exacerbate the very condition being treated. The novel finding, as above set forth, in respect of the present compounds is thus completely against current teaching regarding the pharmacological profile of and utilities for morphine and the like.

In formula (I), as set forth above, $R^1$ is hydrogen, alkyl of 1 or 2 carbon atoms or an amidino group, $R^2$ is alkyl of 1 or 2 carbon atoms, $R^3$ is hydrogen or carbamyl, $X^2$ is a D-radical having the structure:

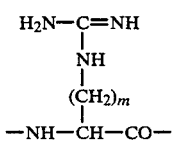

$Z^1$ and $Z^2$ are the same or different and each is hydrogen, halo, nitro or trifluoromethyl and at least one is other than hydrogen, m is 2, 3 or 4 and n is 0, 1 or 2, provided that when $R^3$ is carbamyl then n is always 1, together with pharmaceutically acceptable salts thereof.

Specific identities for $X^2$ are the followign D-radicals: 2—amino—4—guanidinobutyryl (m is 2), arginyl (m is 3) and homoarginyl (m is 4).

The halo identities for $Z^1$ and $Z^2$ may be selected from fluoro, chloro, bromo and iodo.

As subclasses of peptides within formula (I) may be mentioned those wherein:

(i) $R^1$ is an amidino group
(ii) $R^2$ is ethyl
(iii) $R^3$ is hydrogen
(iv) $X^2$ is D-arginyl
(v) one of $Z^1$ and $Z^2$ is hydrogen and the other is fluoro in the 2-position
(vi) n is 0, together with pharmacologically acceptable salts thereof.

A preferred peptide within formula (I) is

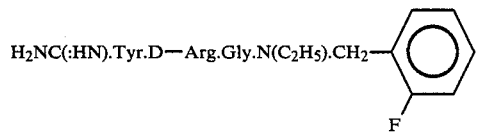

together with pharmacologically acceptable salts thereof; a preferred said salt is the diacetate.

The abbreviations used herein for amino acids and their radicals are those conventional in the art and may be found in, for example, Biochem. J. (1972) 126, 773–780. In the above and throughout the following all references are to the L-configuration of chiral amino acids and their radicals unless otherwise stated.

In the salts of the peptides the biological activity resides in the peptide moiety and the identity of the acid is of lesser importance although for use in medicine it should be pharamacologically acceptable to the recipient. Examples of pharmacologically acceptable acids include mineral acids such as hydrochloric, hydrobromic, phosphoric, metaphosphoric, nitric and sulphuric acids and organic acids such as tartaric, acetic, citric, malic, lactic, fumaric, benzoic, glycollic, gluconic, gulonic, succinic and arylsulphonic, for example p-toluenesulphonic, acids.

The peptides of formula (I) and their salts may be prepared by methods known in the art, in particular those methods taught in the previously identified EP-A-0 127 154.

All references identified hereinabove or in the following are hereby incorporated herein by reference thereto.

The peptides of formula (I) and their salts may be used in both human and veterinary medicine in circumstances such as those previously identified where it is desirable to reverse (i.e. treat) neuronally—mediated bronchoconstriction, and may be administered either on a regular maintenance basis or for the relief or amelioration of acute crisis states.

The peptides and salts thereof may be administered to the human or nonhuman mammalian recipient by a route selected from oral, parenteral (including subcutaneous, intradermal, intramuscular and intravenous), rectal, topical (including dermal, buccal and sublingual), nasal and pulmonary. The size of an effective, bronchodilator dose will depend upon a number of factors including the identity of the recipient, the precise condition to be treated and its severity and the route of administration and will ultimately be at the discretion of the attending physician or veterinarian.

An effective dose for a human being will generally be in the range 0.1 to 50 mg., more generally in the range 0.2 to 25 mg. and most often in the range 0.5 to 12.5 mg., a particularly suitable dose being 1 mg. (all doses calculated as the peptide per se: for salts the figures would be adjusted proportionately). Administration of such doses may be repeated as required throughout the day, for example three or four times a day. For veterinary use, for example in the treatment of non-human mammals such as cats, dogs, cattle, sheep, pigs and horses, the above-recited doses would be increased or decreased at the discretion of the veterinarian having regard to the weight and identity of the recipient.

While it is possible for the compounds to be administered as the raw chemical it is preferable to present them as a pharmaceutical formulation preparation comprising a peptide of formula (I), as above defined, or a pharmacologically acceptable salt thereof together with one or more acceptable carriers therefor and optionally other therapeutic ingredients. The carrier(s) must be 'acceptable' in the sense of being compatible with the other ingredients of the formulation and not deleterious to the recipient thereof.

The formulations include those suitable for oral, parenteral (including subcutaneous, intradermal, intramuscular and intravenous), rectal, topical (including dermal, buccal and sublingual), nasal and pulmonary administration although the most suitable route may depend upon for example the condition and identity of the recipient. The formulations may conveniently be presented in unit dosage form and may be prepared by any of the methods well known in the art of pharmacy. All methods include the step of bringing into association the peptide or salt (the active ingredient) with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral, parenteral, rectal and topical administration are taught in EP-A-0 127 154.

Formulations suitable for pulmonary administration via the buccal cavity are presented such that particles containing the active ingredient and desirably having a diameter in the range 0.5 to 7 microns are delivered into the bronchial tree of the recipient.

As one possibility such formulations are in the form of finely comminuted powders which may conveniently be presented either in a pierceable capsule, suitably of for example gelatin, for use in an inhalation device, or alternatively as a self-propelling formulation comprising active ingredient, a suitable liquid propellant and optionally other ingredients such as a surfactant and/or a solid diluent. Self-propelling formulations may also be employed wherein the active ingredient is dispensed in the form of droplets of a solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example 50 to 100 microliters, upon each operation thereof.

As a further possibility the active ingredient may be in the form of a solution for use in an atomizer or nebulizer whereby an accelerated airstream or ultrasonic agitation is employed to produce a fine droplet mist for inhalation.

Formulations suitable for nasal administration include presentations generally similar to those described above for pulmonary administration. When dispensed such formulations should desirably have a particle diameter in the range 10 to 200 microns to enable retention in the nasal cavity this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of the active ingredient in aqueous or oily solution.

Preferred unit dosage formulations are those containing an effective dose, as hereinabove recited, or an appropriate fraction thereof, of the active ingredient.

EP-A-0 127 154 contains no invitation to administer the present compounds by the nasal or pulmonary route nor any suggestion that the said compounds, if administered in such a manner, would be effective in the treatment of the conditions therein taught; the said disclosure likewise contains no description of any formulation suitable for administration by the nasal or pulmonary route.

Without being limited by theory, the peptides of formula (I) and their pharmacologically acceptable salts may in addition reverse the airway inflammation found in asthma (including status asthmaticus) and postulated also to be neuronal in origin.

The following Examples are provided in illustration of the present invention and should not be construed as in any way constituting a limitation thereof. All temperatures are in degrees Celsius.

Pharmaceutical Formulations

In the following the "Compound" is a pharmacologically acceptable salt of a peptide of formula (I) as hereinbefore defined, the weight thereof being calculated as the peptide per se.

| Capsule | |
|---|---|
| Compound | 1.0 mg |
| Magnesium stearate | 0.75 mg |
| Lactose BP to | 200.0 mg |

Mix the ingredients and fill into hard gelatin capsules, each to contain 1.0mg of compound.

| Tablet | |
|---|---|
| Compound | 1.0 mg |
| Avicel PH 101 | 22.5 mg |
| Low-substituted hydroxypropylcellulose | 9.0 mg |
| Polyvinylpyrrolidone K30 | 6.0 mg |
| Magnesium stearate | 0.75 mg |
| Lactose BP to | 150.0 mg |

| Freeze-Dried Injection | |
|---|---|
| Compound | 1.0 mg |

| -continued | |
|---|---|
| Freeze-Dried Injection | |
| Mannitol | 62.5 mg |
| Water for Injections to | 2.5 ml |

Dissolve the mannitol and compound in 9/10 the total quantity of water and make to volume when solution is complete. Under sterile conditions, sterilise the solution by filtration through a suitable, sterile, sterilising grade filter and pack into clean, sterile vials using a fill of 2.5ml per vial. Partially insert freeze drying stoppers into the necks of the vials and freeze dry. Close the vials under an inert gas and secure with aluminium collars.

| Suppository | |
|---|---|
| Compound | 1.0 mg |
| Hard Fat BP to | 1000.0 mg |

| Dermal Lotion | |
|---|---|
| Compound | 0.1 g |
| Sorbitan monolaurate | 0.6 g |
| Polysorbate 20 | 0.6 g |
| Cetostearyl alcohol | 1.2 g |
| Glycerin | 6.0 g |
| Methyl p-hydroxybenzoate | 0.2 g |
| Purified Water BP to | 100.0 ml |

Dissolve the methyl p-hydroxybenzoate and glycerin in 70ml of the water at 75° C.; melt together the sorbitan monolaurate, polysorbate 20 and cetostearyl alcohol at 75° C. and add to the aqueous solution. Homogenise the resulting emulsion, allow to cool with continuous stirring and add the compound as a solution in the remaining water; stir the product until homogeneous.

| Solution for nebulisation | |
|---|---|
| Compound of formula (I) (calculated as peptide per se) | 1.0 mg |
| Water for injections to | 10.0 ml |

Dissolve the compound of formula (I) in the water for injections. Sterilize the solution by passage through a membrane filter, 0.2 μm pore size, collecting the filtrate in a sterile receiver. Fill into sterile glass ampoules, 10 ml/ampoule, under aseptic conditions and seal each ampoule by fusion of the glass.

| Self-propelling formulation | |
|---|---|
| Compound of formula (I), micronised (calculated as peptide per se) | 1.0 mg |
| Propellant to | 5.0 ml |

Suspend the micronised compound of formula (I) in the propellant. Fill this suspension under pressure into preformed, valved aerosol canisters, 5 ml/canister, through the valve orifice.

The propellant is a commercially available mixture of trichloromonofluoromethane, dichlorodifluoromethane and dichlorotetrafluoroethane.

| Powder for inhalation | |
|---|---|
| Compound of formula (I), micronised (calculated as peptide per se) | 1.0 mg |
| Lactose | 29.0 mg |

Triturate and blend the micronised compound of formula (I) with the lactose. Fill the resulting powder blend into hard gelatin capsule shells, 30 mg per capsule.

| Nasal drops | |
|---|---|
| Compound of formula (I) (calculated as peptide per se) | 100 mg |
| Methyl p-hydroxybenzoate | 10 mg |
| Water for injections to | 10 ml |

Dissolve the compound of formula (I) and the methyl p-hydroxybenzoate in the water for injections. Fill this solution into suitable dropper bottles, 10 ml/bottle, and close by securing the dropper nozzle and bottle cap.

What we claim is:

1. A method of treating neuronally-mediated bronchoconstriction in a mammal suffering from same, which comprises administering to said mammal an effective, non-toxic, bronchodilator amount of a peptide of formula (I)

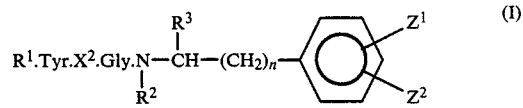

wherein
$R^1$ is hydrogen, alkyl of 1 or 2 carbon atoms or an amidino group,
$R^2$ is alkyl of 1 or 2 carbon atoms,
$R^3$ is hydrogen or carbamyl,
$X^2$ is a D-radical having the structure:

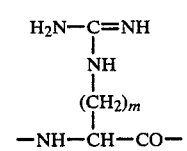

$Z^1$ and $Z^2$ are the same or different and each is hydrogen, halo, nitro or trifluoromethyl and at least one is other than hydrogen,
m is 2, 3 or 4 and
n is 0, 1 or 2,
provided that when $R^3$ is carbamyl then n is always 1, or a pharmacologically acceptable salt thereof.

2. The method of claim 1 which comprises administering the peptide

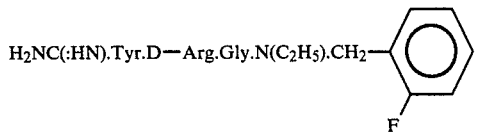

or a pharmacologically acceptable salt thereof.

3. The method of claim 2 which comprises administering a pharmacologically acceptable salt of the peptide.

4. The method of claim 2 which comprises administering the diacetate salt of the peptide.

5. The method of claim 1 which comprises administering the peptide or salt by the oral route.

6. The method of claim 1 which comprises administering the peptide or salt by the parenteral route.

7. The method of claim 1 which comprises administering the peptide or salt by the rectal route.

8. The method of claim 1 which comprises administering the peptide or salt by the topical route.

9. The method of claim 1 which comprises administering the peptide or salt by the nasal route.

10. The method of claim 1 which comprises administering the peptide or salt by the pulmonary route.

11. The method of claim 1 which comprises administering the peptide or salt in a pharmaceutically acceptable carrier therefor.

12. The method of claim 1 in which the mammal is a human being.

13. The method of claim 1 in which the mammal is a human being suffering from asthma.

* * * * *